United States Patent [19]

Hepburn

[11] Patent Number: 4,657,000
[45] Date of Patent: Apr. 14, 1987

[54] ADJUSTABLE SPLINT AND SECURING MEANS THEREFOR

[75] Inventor: George R. Hepburn, Severna Park, Md.

[73] Assignee: Dynasplints Systems, Inc., Baltimore, Md.

[21] Appl. No.: 638,766

[22] Filed: Aug. 8, 1984

Related U.S. Application Data

[60] Division of Ser. No. 484,439, Apr. 13, 1983, Pat. No. 4,508,111, which is a continuation-in-part of Ser. No. 367,598, Apr. 12, 1982, Pat. No. 4,485,808, and a continuation-in-part of Ser. No. 286,161, Jul. 23, 1981, Pat. No. 4,397,308.

[51] Int. Cl.$^4$ .............................................. A61F 3/00
[52] U.S. Cl. .................................... 128/88; 128/87 R
[58] Field of Search ............... 128/DIG. 15, 87 R, 88; 24/446, 442, 445; 2/124, 256

[56] References Cited

U.S. PATENT DOCUMENTS

| 2,661,000 | 12/1953 | Gazeley et al. | 128/88 |
| 3,387,345 | 6/1968 | Savoir | 24/446 |
| 3,548,817 | 12/1970 | Mittasch | 128/87 R |
| 4,215,687 | 8/1980 | Shaw | 128/DIG. 15 |

FOREIGN PATENT DOCUMENTS

| 830507 | 3/1960 | United Kingdom | 128/80 F |
| 972648 | 10/1964 | United Kingdom | 24/446 |

Primary Examiner—Stephen F. Husar
Attorney, Agent, or Firm—Larson and Taylor

[57] ABSTRACT

An adjustable spring-loaded splint comprising a pair of lower struts and a pair of upper struts, each member of the pair of lower struts being pivotably connected to a member of the pair of upper struts, said members of each pair being spaced apart a distance to accommodate limb parts distal and proximal to the limb joint, at least one of said struts having at one end a pivotably mounted head portion defining a cam surface, an adjustable spring means mounted within the strut pivotably connected to said cam surface-containing strut and biased into engagement with said cam surface, for applying a quantifiable force tending to aling or approximate the cam surface-containing strut with the adjustable spring means and means provided said pair of upper struts and said pair of lower struts for securely holding therebetween said distal and proximal parts of a limb. A securing means comprising an elongate cuff member having on the outside thereof at least one velcro loop section spaced apart from at least one velcro hook section, said loop and hook sections each being followed by a zone therebetween containing both velcro hook and velcro loop sections, said zone between the spaed apart velcro hook and loop sections being comprised of an intermediate area constituted of a velcro loop section or hook section identical to the preceding section, flanked on each side by areas having a velcro loop section or a velcro hook section identical to the section of velcro hooks or loops that follows.

2 Claims, 11 Drawing Figures

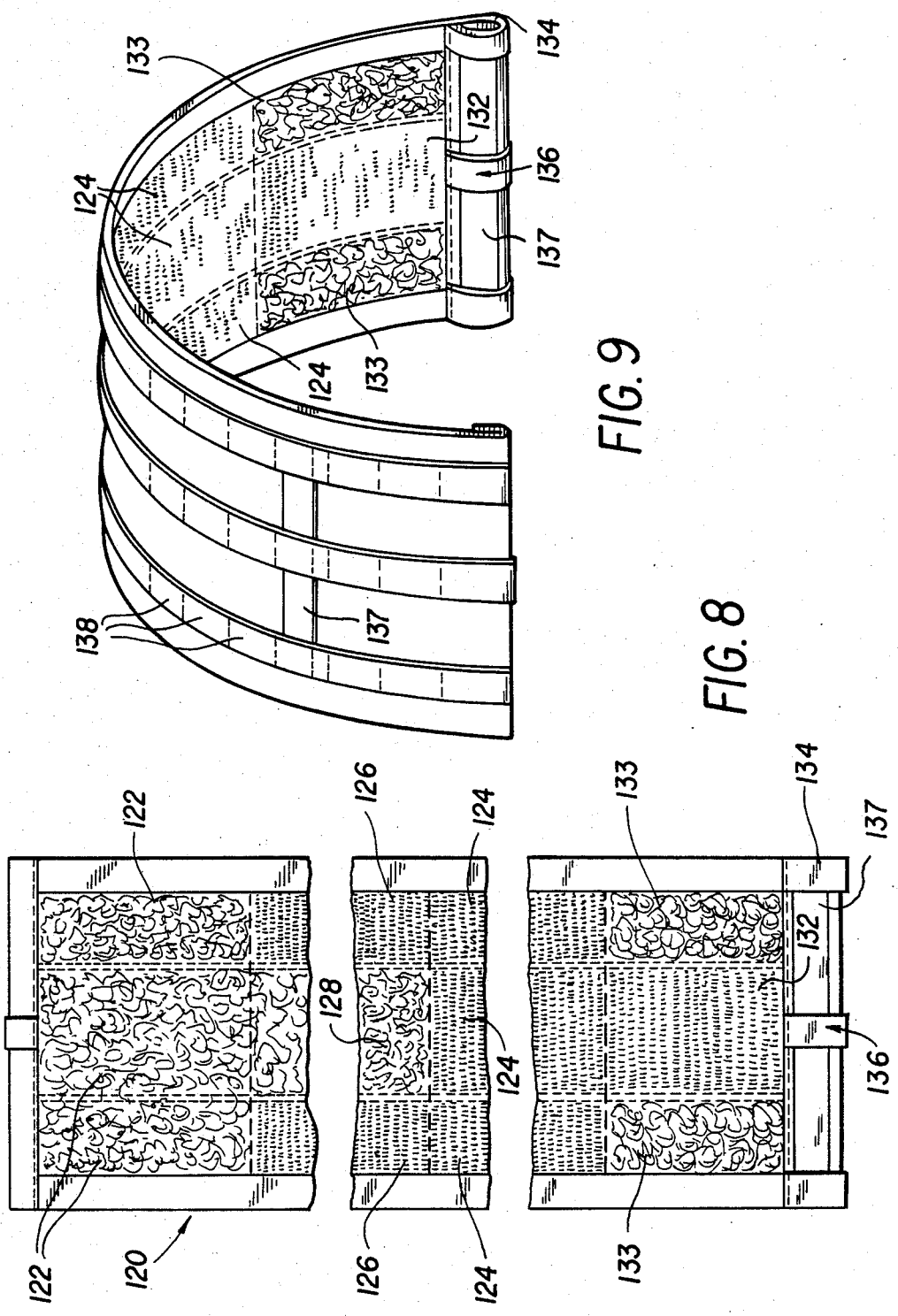

ADJUSTABLE SPLINT AND SECURING MEANS THEREFOR

This is a division of application Ser. No. 484,439, filed Apr. 13, 1983, now U.S. Pat. No. 4,508,111, which is a continuation-in-part of application Ser. No. 367,598, filed Apr. 12, 1982, now U.S. Pat. No. 4,485,808 and a continuation-in-part of application Ser. No. 286,161, filed July 23, 1981, now U.S. Pat. No. 4,397,308.

BACKGROUND OF THE INVENTION

1. Field of the Invention

This invention relates to an adjustable splint. More particularly, this invention relates to an adjustable splint useful in treating impairments in body joints such as knees, elbows, wrists, fingers, backs and the like from flexion or extension contracture, weakness in the supporting musculature, or some other malady inhibiting the integrity of the body joint in accomplishing extension or flexion.

2. Prior Art

There are cases too numerous to mention wherein bedridden individuals have lost ambulation simply from developing a knee flexion contracture. The various causes of developing knee flexion contractures in this segment of the population is many fold. Very frequently, dissuse and neglect of an existing medical problem such as a stroke, fractures about the knee or vascular problems, just to mention a few, will result in the development of a knee flexion contracture. In addition, people having any type of knee surgery, especially medial menisectomies, open reduction and internal fixation of a fracture and ligamentous repairs, all enter into the possibility of developing a knee flexion contracture. There are also other injuries about the knee not requiring surgery which develop into knee flexion contractures. These injuries include meniscal tears, ligament tears (both partial and complete) and fractures about the knee which are reduced by close reduction. If these knee flexion contractures, whatever their cause, could be reduced, more than 50% of all bedridden patients having knee flexion contractures would gain tremendous progress toward gaining independence in ambulation.

People also develop extension contractures in the fingers, wrists, elbows, knees and other joints from many and various causes. Weakness, disuse, fractures, surgeries, traumatic injuries, illness and other causes have been known to cause loss of ability to flex the body joint otherwise known as an extension contracture. No device presently exists to reduce extension contractures by adjustable, quantifiable pressure as does the adjustable splint for flexion described herein.

Many splint devices and mechanisms have been designed to be influential at the knee either for support or for mobilizing the knee joint. Illustrative of such devices are those described in U.S. Pat. Nos. 3,055,359; 3,928,872; 3,785,372 and 3,799,159. However, all of these devices are not designed to reduce knee flexion or extension contractures or cannot be tolerated by the patient population for a long enough period to effectively reduce a contracture. Moreover, none of the devices offer a satisfactory means for adjusting the pressure exerted by the lateral struts of the splint devices.

OBJECTS OF THE INVENTION

Accordingly, it is an object of the invention to provide an improved splint device for reducing flexion or extension contractures about a body joint such as a knee, elbow, finger or wrist.

Another object of the invention is to provide a splint device which will shorten the rehabilitation time of individuals that are bedridden or incapacitated due to flexion or extension contractures about a joint.

Yet another object of the invention is to provide a splint device, which allows easy gradual adjustment to the quantifiable force desired on an extremity acting across a body joint.

A further object of the invention is to provide a splint device for incarcerated patients to help obtain a higher level of independence in their activities of daily living, self care and ambulatory activities.

A further object would be to provide an improved splint for providing support to a limb around a body joint such as a knee, elbow, wrist or finger, in cases where muscular weakness exists.

SUMMARY OF THE INVENTION

These and other objects of the invention are obtained by an adjustable splint assembly comprising a lower strut and an upper strut pivotably connected to said lower strut, one of said struts having at one end a pivotably mounted head portion defining a cam surface, an adjustable biasing means mounted within the other strut and biased into engagement with said cam surface, for applying a quantifiable force tending to approximate or align said upper and lower struts and means for securing said splint assembly to a limb.

In a preferred embodiment the present invention comprises a pair of lower struts and a pair of upper struts, each member of the pair of upper struts, said members of each pair being spaced apart a distance to accomodate limb parts distal and proximal to the limb joint, at least one of said struts having at one end, a pivotably mounted head portion defining a cam surface, an adjustable biasing means mounted within the strut pivotably connected to said cam surface-containing strut and biased into engagement with said cam surface, for applying a quantifiable force tending to align or approximate the cam surface-containing strut with the adjustable biasing means containing strut and means provided said pair of upper struts and said pair of lower struts for securely holding therebetween said distal and proximal parts of a limb.

In one aspect of the invention the splint device is provided with telescoping wire assembly on the upper and lower struts whereby the splint device is secured to the limbs. This slidably adjustable wire assembly feature enables the splint device of the invention to accomodate various limb lengths. In addition, novel snap-on comfort pads attachable to the struts of the splint device provide greater patient comfort.

Another aspect of the invention involves a novel cuff for attaching the splint device to a limb which cuff is designed to accomodate limbs of varying circumference.

BRIEF DESCRIPTION OF THE DRAWINGS

The invention will appear more clearly from the following detailed description when taken in connection with the following drawings which show by way of example a preferred embodiment of the invention:

In the drawings:

FIG. 8 is a plan view of the outside of another cuff for attachment to the wire assembly designed to accomodate limbs of varying circumferences;

FIG. 9 is a perspective view of the cuff shown in FIG. 9;

DESCRIPTION OF THE PREFERRED EMBODIMENT

Figure 1:
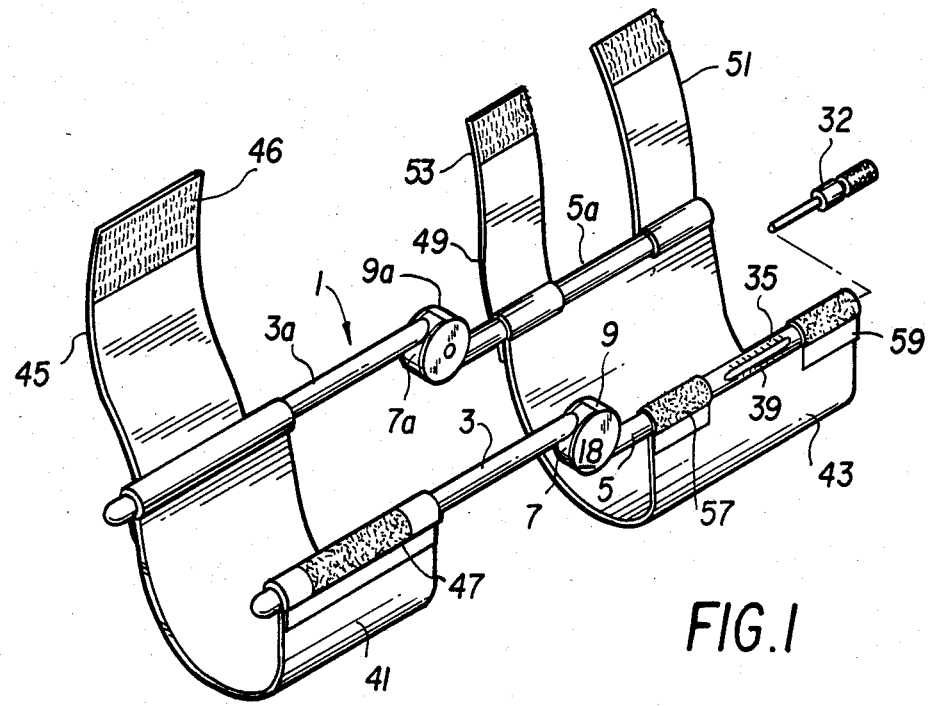
FIG. 1 is a perspective view of the adjustable splint for reducing flexion contractures.
Figure 2:
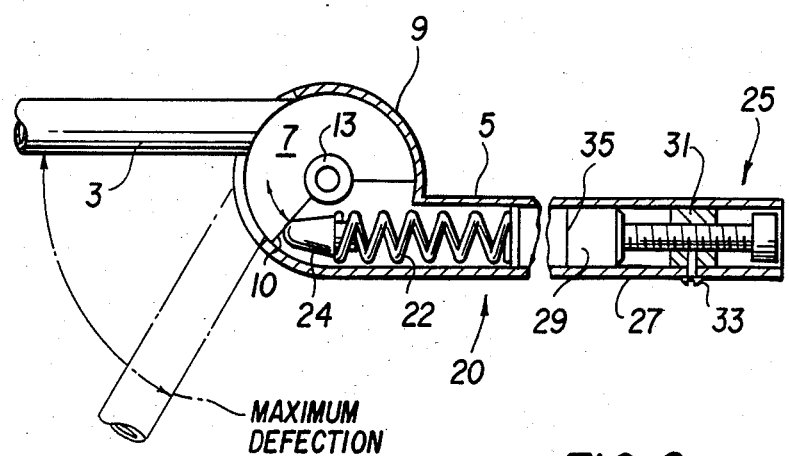
FIG. 2 is a perspective view of one upper and one lower strut assembly of the adjustable splint of the invention for reducing flexion contractures wherein a strut is broken away to show the adjustable spring-loaded means mounted therein.
Figure 3:
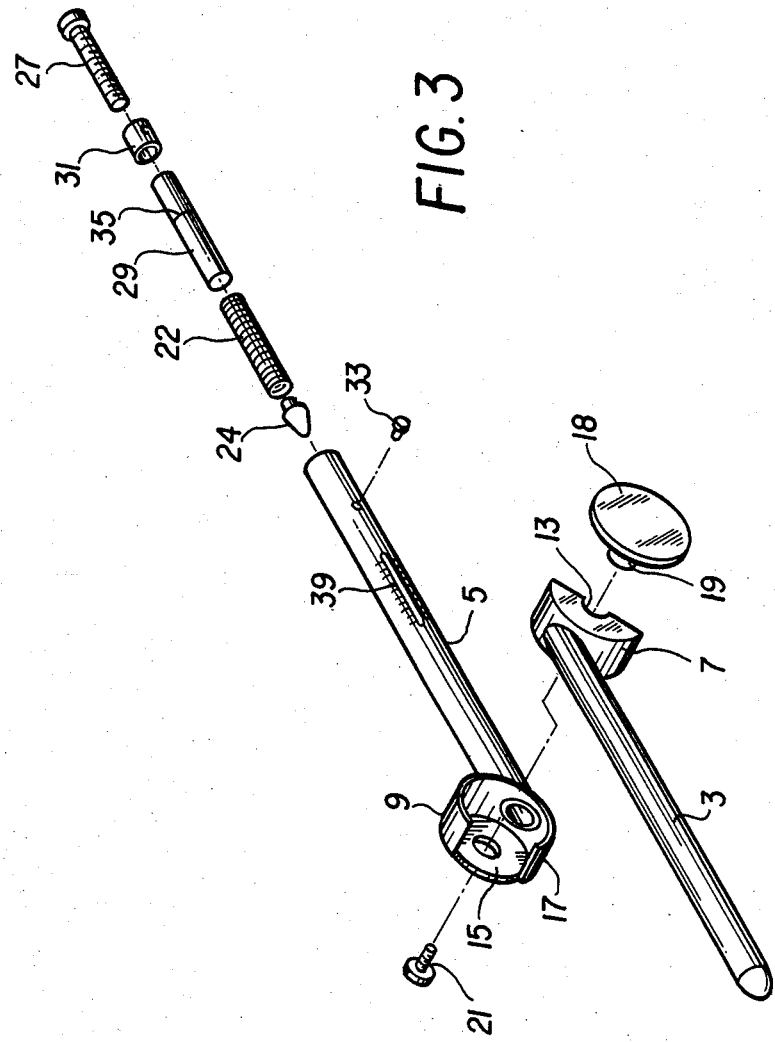
FIG. 3 is a perspective, exploded view of the splint device of FIG. 1.

Referring to FIGS. 1-3, an adjustable splint device 1 is comprised of lower struts 3 and 3a and upper struts 5 and 5a. Lower strut 3 contains a rounded head portion 7 and upper strut 5 contains a socket head portion 9 which receives head portion 7 for pivotable engagement therewith. Rounded head portion 7 is cut away to define a cam surface 10 and is provided with an axial surface recess 13. A first surface plate 15 having a screw hole 17 covers one side of the combined head portions 7-9 and a second plate member 18 having a threaded protruding member 19 (see FIG. 3) covers the other half of the combined head portion 7-9. When surface plate member 18 is positioned over the combined head portion 7-9 protruding member 19 projects through the axial circular recess 13 and receives a screw 21 through screw hole 17. Lower strut 3a and upper strut 5a are similarly pivotably connected by corresponding members bearing like numbers but carrying the distinguishing suffix "a".

Figure 7:
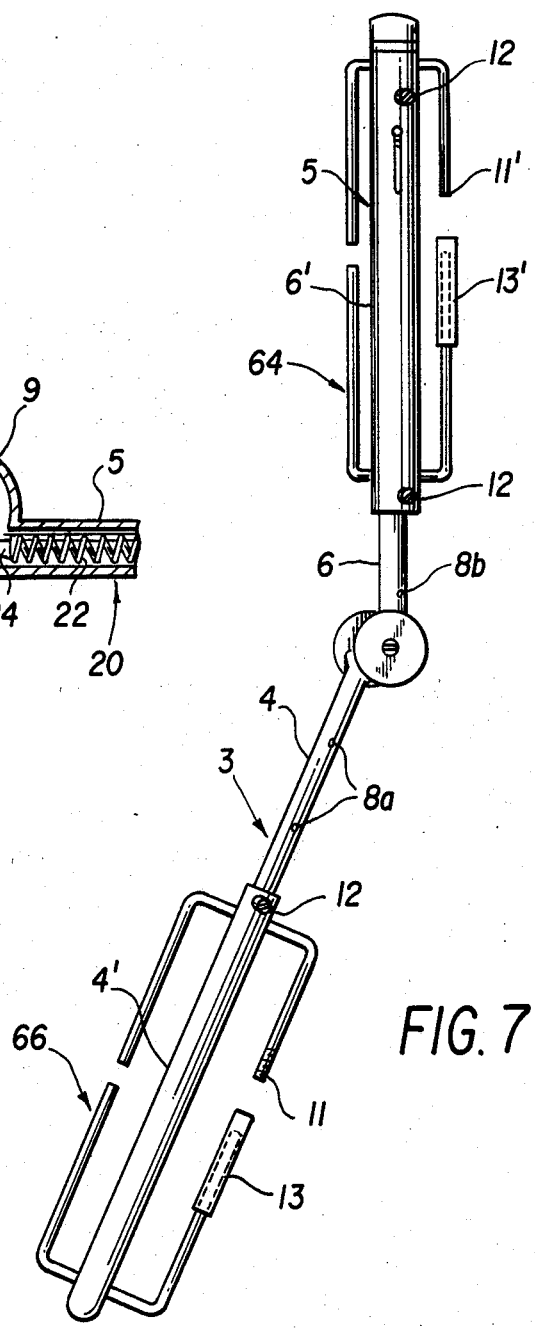
FIG. 7 is a perspective view of the splint device provided with a telescoping slidably adjustable wire assembly for mounting of the means by which the device is secured to the limb.

The lower and upper struts may be constructed of any material of sufficient strength such as plastic, metal, wood and the like. Particularly preferred are struts made of stainless steel metal. At least one of the struts should be at least partially hollow so as to house therein the adjustable spring mechanism of the invention. Most advantageously, all of the struts are tubular in construction so as to provide a lightweight product. Preferably each of the struts 3, 3a, 5 and 5a can be comprised of two telescoping portions as shown in the single strut depicted in FIG. 7 so as to permit lengthening and shortening of the struts. Directing attention to FIG. 7, strut 3 is comprised of telescoping portions 4 and 4', strut 5 of telescoping portions 6 and 6'. The inner portions 4 and 6 are provided with a series of threaded holes 8 and 8a and the outer portions 4' and 6' with holes and threaded holes, respectively, through which screws 12 pass for threaded engagement with a coincident hole 8 and 8a. Where the distal strut is of larger diameter than the proximal strut as shown in FIG. 7 it is preferable to provide threads in the holes of the outer portion 6'. Such a telescoping feature provides a splint which can be adjusted to several different lengths allowing the splint to fit a greater number of individuals. It should be understood that in this embodiment the splint device combination of the invention will include a series of spring abutting members 20 (see FIG. 3) of varying lengths so as to accomodate different limb lengths.

The adjustable spring-loaded mechanism designated generally as 20 may be provided in either the lower or the upper struts. Preferably, only the lower struts 5 and 5a are provided with the adjustable spring mechanism.

Figure 6:
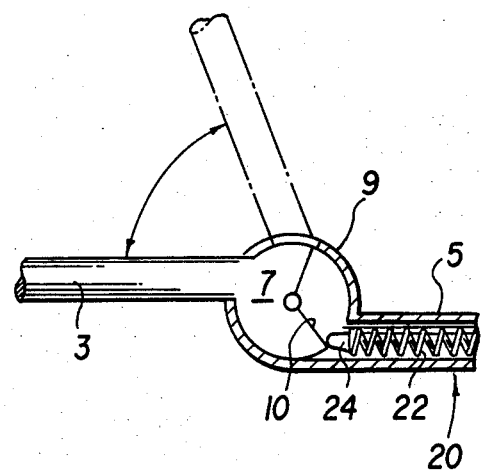
FIG. 6 is a perspective view of one upper and one lower strut assembly of the adjustable splint of the invention for reducing extension contractures wherein a strut is broken away to show the adjustable spring-loaded means mounted therein.

The adjustable spring mechanism 20 is comprised of a spring 22 to which is attached a nose element 24 that bears on cam surface 10. Coil or clock springs are generally preferred but in some instances leaf springs are advantageously employed, particularly in small devices such as finger or wrist splints. An adjustable screw means indicated generally as 25 abuts the other end of the spring 22 and produces a quantifiable force which tends to either extend, (i.e. align the lower strut 5 with the upper strut 3 and lower strut 5a with upper strut 3a in a parallel fashion) as shown in FIG. 2 or to approximate (i.e. bring together the lower strut 5 with the upper strut 3 and lower strut 5a with upper strut 3a) as shown in FIG. 6. As maximum deflection or flexion is approached, tension is created in the compression coiled spring 22. The adjustable screw means 25 is comprised of an "Allen" head screw or slotted head screw 27 threaded to a spring-abutting member 29. The "Allen" head screw is fixed within upper strut 3 by screw 33. The "Allen" head screw 27 receives and is turned by an "Allen" socket wrench 32 (see FIG. 1) whereas a slotted head screw is adjustable with a conventional screwdriver blade. The turning of the screw creates greater compression of spring 22 thereby exerting greater force on the cam surface 10 of the lower strut 5 to exert a one way tension. The tension capability of the spring mechanism can range from 0 pounds tension up to the maximum tension capable of the spring. In general, the tension of the spring mechanism will range from 0 pounds tension up to 10 pounds of tension and the tension exerted by the spring can be varied at any point of joint range of motion, say from 60° flexion to 0° flexion of the joint.

Whereas the specific joint range of motion to which tension can be exerted is preferred to be 65° flexion through 0° flexion for reducing flexion contractures in the knee and elbow, the joint range of motion at which tension can be applied can vary to nearly any degree in the 360° circular range simply by varying the point of attachment of the inner portion of strut 3 to rounded head portion 7 and by varying the point of attachment of the inner portion of strut 5 to socket heat portion 9. Likewise, the same variations apply to struts 3a and 5a.

The purpose of varying the point in the joint range to which tension is applied is obvious when you consider that different illnesses and injuries cause different types of limitations at different degrees of joint ranges of motion thereby making necessary different points in the joint range at which tension must be applied to improve their condition. Another example would be when reducing an extension contracture of the knee the desired range of motion to which tension would be applied would range from 40° flexion to 130° flexion. The spring mechanism can be calibrated to exert this range of tension. The calibration can be effected by providing spring-abutting member 29 with a poundage indicator line 35 and a calibration scale 37 about the lower strut 5 which scale has a slot 39 through which the poundage indicator 35 is visible.

While the preferred adjustable biasing means of the invention is a spring means such as described, equivalent biasing means such as air or hydraulic powered biasing means will readily come to the mind of those skilled in this art.

Any suitable means can be utilized to secure pivotably mounted struts 3 and 5 and pivotably mounted struts 3a and 5a to the limb so that they lie lateral to the joint with the axis of rotation coinciding as closely as possible to the axis of rotation of the joint. As shown in the figures, the securing means comprise a proximal cuff 41 attached to and extending between upper strut 3a and upper strut 3 and distal cuff 43 attached to and extending between lower strut 5a and lower strut 5. The length of the proximal cuff 41 and distal cuff 43 is of sufficient distance to comfortably accomodate the limb parts distal and proximal to the limb joint. An overlying flap 45 is attached at one end to upper strut 3a and contains on its outer surface an attaching means such as velcro hooks 46 by which the flap can wrap about the proximal portion of the limb and be secured to the velcro loops 47 on the outer surface of the proximal cuff wrapped about upper strut 3. Distal cuff 43 is secured to lower strut 5a and 5 and contains two separate flaps 49 and 51 each containing on their outside velcro attaching loops 53 and 55 respectively. The flaps 49 and 51 are of sufficient length to extend over and secure the limb portion lying in distal cuff 43 by attachment to the velcro loops receiving areas 57 and 59 provided on the distal cuff 43 about the lower strut 5.

It should be understood that a single combined strut, such as upper strut 3 pivotably connected to lower strut 5, can alone be utilized as a splint device by securing same by suitable means to the lateral side of the limb to be treated. Again, any suitable means for strapping or securing the splint device of the invention can be used, for example, by distal and proximal cuffs of sufficient lengths to wrap around the distal and proximal portions of the limb being treated. The straps 45, 49 and 51 as well as the cuffs 41 and 43 can be secured to the struts in any suitable manner as by sewing, tying, etc.

Figures 4, 5:
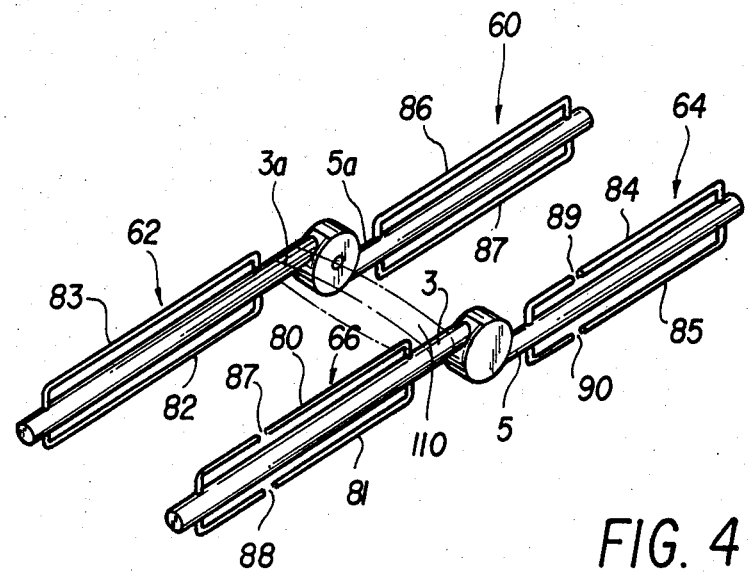
FIG. 4 is a perspective view of the splint device provided with a "break apart" wire assembly for mounting of the means by which the device is secured to the limb.
FIG. 5 is a cuff designed for attachment to the wire assembly shown in FIG. 4.

To facilitate the attachment of the cuffs and straps, however, it is preferred that wire assemblies, designated generally in FIG. 4 as 60, 62, 64 and 66, be fastened as by welding to struts 5, 5a and 3 and 3a, respectively. The wire assembly 62 is comprised of an upper thin wire portion 83 and a thin wire lower portion 82, each of which wire assembly portions extend from one end of strut 3a to the other. Similarly, wire assembly 60 is comprised of an upper thin wire portion 86 and a lower wire portion 87. In the preferred embodiment shown in FIG. 7 the shorter sides of the wire assemblies are of continuous construction and bent for more secure attachment as by welding to the struts. In the embodiment of FIG. 4 wire assemblies 64 and 66 differ from wire assemblies 60 and 62 in being of the "break apart" type as will be explained below so as to facilitate insertion and removal of the cuffs or straps for cleaning, replacing, etc. Thus, wire assembly 66 is comprised of an upper thin wire portion 80 and a lower thin wire portion 81 both of which are broken at 87 and 88, respectively, so that the wire can be pulled apart slightly when the cuff or straps are to be attached or removed. Similarly, wire assembly 64 is comprised of a thin upper wire section 84 and a thin lower wire section 85 both of which are broken at 89 and 90, respectively. In the embodiment of FIG. 7, however, all of the wire assemblies are of "break apart" type but one, wire portion on both the distal and proximal struts, that is, two of the four receiving wires contains telescoping sections B and B'. Telescoping sections B and B' are internally threaded at one end for engagement with threaded end 11 and 11' or the wire portion. This gives the wire fixture added strength. Normally a wire assembly with telescoping sections B and B', however, is only used on the side of the strut which makes an angle of 65° when flexed.

When the adjustable splint is to be used for extension of a joint, a strap 110 is provided between struts 3 and 3a as shown in FIG. 4 and between 5 and 5a. Use of a strap 110 both between struts 3 and 3a and 5 and 5a is often advisable in many instances particularly in reducing knee flexion contractures. Strap 110 in these applications is important in order to maintain optimal alignment of the upper and lower struts along the parallel of the limb part proximal and distal to the joint. Strap 110 also helps maintain the axis of rotation of the splint joint assembly more coincident with the axis of rotation of the body joint to which the splint is being applied.

Attachment of cuff 92, provided with velcro hooks section 98 and a velcro loop section 100 as shown in FIG. 5, to the wire assemblies shown in FIG. 4 may then be conducted in the following manner:

Loop end section 94 of cuff 92 is put on wire portion 80 via break 87 with the velcro hooks section 98 and velcro loop section 100 facing outward. Edge 96 is taken over the limb and fed through and under wire portion 83 of wire assembly 62, and then put back on itself whereby velcro hooks 98 adhere to velcro loops 100. This secures one of the four cuffs needed to fix the splint assembly to a limb about a joint. A cuff is attached to wire sections 84 and 86 in a similar manner. The same procedure is used to attach cuffs or straps to the wire sections 81–82 and wire sections 85–87.

Where but a single assembly of an upper and lower strut is to be used the respective cuffs and straps are provided near their ends with suitable securing means such as velcro hooks and loops. It should be understood that while the securing means are shown to be velcro closures other alternative closures, such as snaps and the like can be provided the straps and cuffs.

Another novel cuff which can be used to secure the splint device to the limb is shown in FIGS. 8 and 9. Referring to these figures the cuff 120 is of a length sufficient to accomodate limb parts distal and proximal to the limb joint. The outside of cuff 120 is composed of a spaced apart and alternating velcro loop section 122 and a velcro hook section 124 each followed by a zone therebetween containing both velcro hook sections and velcro loop sections. Most advantageously the zones containing both hook sections and loop sections are comprised of an intermediate area 128 constituted of a velcro loop or hook section identical to the preceding section flanked on each side by areas having velcro loop or hook sections identical to the section of uniform velcro hooks or loops that follows. Thus, in FIG. 8 the zone following velcro loop section is composed of an intermediate velcro loops area 128 flanked on each side by velcro hook areas 126. Velcro hook section 124, on the other hand, is followed by a zone having velcro hook area 132 flanked by velcro loop areas 133. If a longer cuff is required the next zone would be of velcro loops only, etc.

Loop end section 134 of cuff 120 is provided with a stay-receiving means indicated generally as 136 into which is inserted a plastic stay 137 to prevent any collapsing that is likely to occur during use. Also, the inside of cuff 120 contains multiple stay receiving means 138. The cuff is shown in the figures as rectangular in shape. It should be understood, however, that the cuff can assume various curved configurations so as to conform to the particular limb to which it is attached. Attachment of cuff 120 to the wire assembly and the patient limb can be effected as described above.

Figure 10:
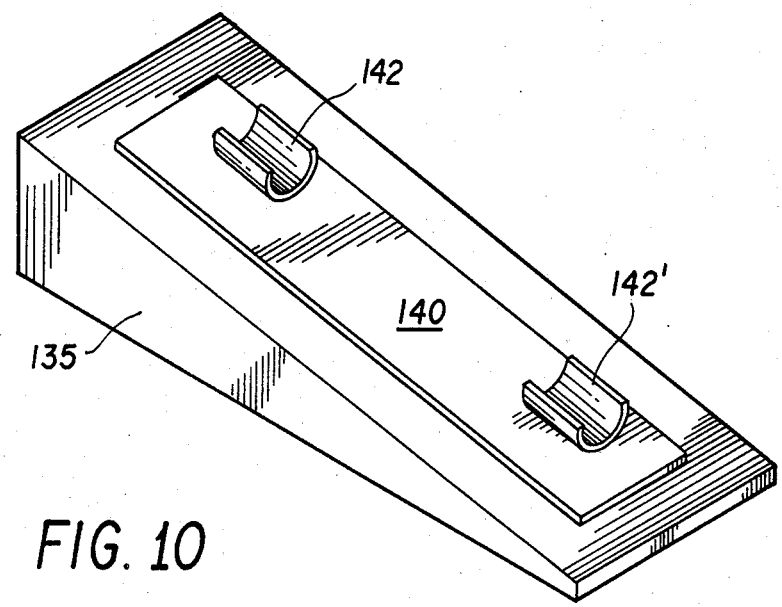
FIG. 10 is a perspective view of a wedge-type comfort pad for use in combination with the adjustable splint of the invention.
Figure 11:
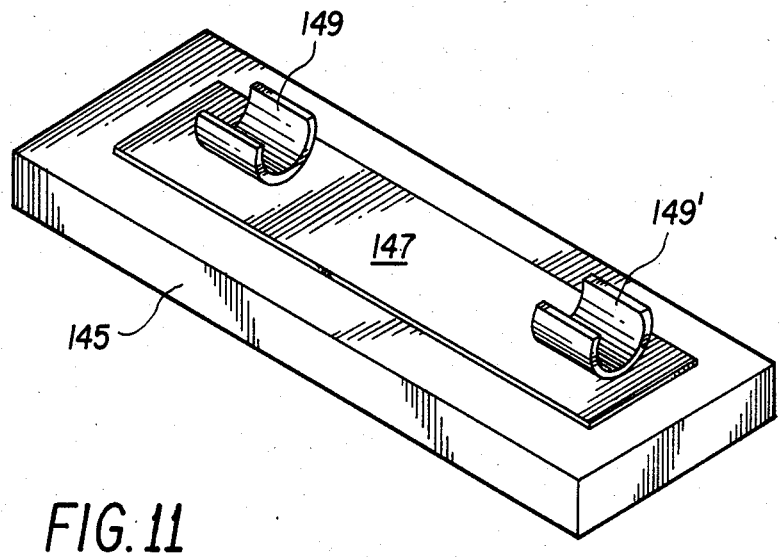
FIG. 11 is a perspective view of a rectangular-type comfort pads for use in combination with the adjustable splint of the invention.

In a preferred embodiment of the invention, the splint device is provided with snap-on comfort pads shown in FIGS. 10 and 11. The comfort pads are of two types, the wedge-type of FIG. 10 and the rectangular-type of FIG. 11. The wedge-type comfort pad of FIG. 10 is composed of a wedge base 135 provided with a snap-on section comprised of a base plate 140 containing spaced snap-on elements 142 and 142'. The rectangular-type comfort pad of FIG. 11 is composed of a base plate 147 and snap-on elements 149 and 149'. The wedge base 135 and rectangular base 145 may be constructed of any suitable light weight material such as foamed plastic. The wedge-type comfort pads are used only when the adjustable splint of the invention is applied to the lower extremities, e.g. thigh and leg. In this instance, two wedge-type comfort pads are normally snapped onto the distal and proximal struts, respectively, within the wire assembly and between the limb and strut in a fashion whereby the thick portion of each wedge is proximal to the point of pivotable engagement of said struts.

The rectangular comfort pads are similarly snapped on the struts within the wire assembly and between the limb and the strut. Where the adjustable splint of the invention is applied to the lower extremities two of the rectangular comfort pads will be placed on the lateral side of the lower extremities, one on the proximal strut and the other on the distal strut. On the other hand, where the adjustable splint is used on the upper extremities, e.g. arms, the rectangular-type comfort pad will be used exclusively. In this case, normally four of the rectangular-type comfort pads will be snapped onto the distal and proximal struts as set forth above, both on the lateral and medial side of the upper extremity.

The unique characteristics of the adjustable spring-loaded mechanism of the present invention is that is allows for adjustment of quantifiable force on an extremity acting across the body joint from 0 foot poundage up to the maximum foot poundage at various body joint ranges.

As an example, in a patient having a knee flexion contracture of 30°, one may want to apply the splint to the knee and build in a tension of 5 foot pounds of force acting on the calf at 30° knee flexion angle. As the patient develops greater tolerance to the device, in days to come, greater force can be adjusted in the mechanism by simply adjusting the "Allen" wrench 32 and causing greater compression to the spring in the strut. This will exert a greater compression to the spring in the strut. This will exert a greater force toward extending the joint which will ultimately serve a more beneficial purpose in accomplishing reduction of the knee flexion contracture. On the other hand, if the patient has a flexion contracture of 45°, the same tension could be dialed into the splint at the angle just as could be done at 30° and just as could be done at a 10° knee flexion contracture. In other words, any force up to maximum capability of the spring employed in the strut can be dialed at any angle of knee flexion. In addition, the invention permits the interchangability of springs bearing force-exerting capabilities so as to allow for varying the degrees of tension exerted by the spring mechanism depending upon the particular use to which the device is applied.

For a person with Quadriceps muscle weakness, heavier gauged spring may be needed to allow for a greater force for extending the knee. In the gait of the person, as they are walking for gait training, the device will allow for knee flexion from 0° to maximum flexion while forcing the knee back toward extension at the top of the swing phase of the gait. This will accomodate for weakness in the Quadriceps muscle and prevent collapse of the knee during gait training.

As an example of a particular case in which the adjustable splint for flexion of a joint might be used, one may consider an extension contracture, i.e. loss of ability to flex the joint through the normal range of motion, of any particular body joint such as the knee, elbow, wrist, fingers, etc. For simplicity the knee joint will be used.

In a knee extension contracture, whether the contracture is of a muscle or joint type, the individual may be able to flex the knee to 45° and no further. Applying the adjustable splint for flexion would be useful in that a force would be exerted on the body parts proximal and distal to the knee which would tend to approximate the calf to the posterior thigh. The force exerted by the splint would be adjustable from 0 foot pounds of torque across the knee joint to upward torque of whatever tension capability the particular spring being used would have. Surmising a reasonable force would be to have an upper limit of 10–20 foot pounds acting at mid calf and/or mid thigh. The exact tension desired would be determined by factors such as patient tolerance, type and age of the contracture, skin compliance, diagnosis, etc.

Once the beginning tension and duration of splint application is determined, progression of the tension and duration can be accomplished by simple adjustment of the head screw 27 and increasing time, respectively.

A unique feature of this device in the present application to the knee, and to any body joint, is the ability of this device to allow graduated, quantified, adjustable tension with the ability to relax the stretch across the joint by extending the knee away from the limit of flexion. This will allow the tissue being stretched to have a rest period while not disturbing the adjustment of the spring tension and without having to remove the splint. In order to relieve the pressure of the contractured tissues, one merely has to overcome, by any means, the tension in the splint and extend the joint to a comfortable posture. Once a short rest is achieved, the splint may again exert its tension against the contractured tissue to help accomplish a greater degree of flexion in the joint. In the case of a knee extension contracture, flexion would advance from the point of contracture, say 45° flexion, to the upper theoretical limits of flexion which, binding any other negating factors, would be 135°-150°. Time necessary to accomplish the optimal result using this splint would vary depending on many factors, some of which are the patient's diagnosis, age of patient, age of the contracture and tolerance of the patient.

While the features of this invention have been disclosed with reference to the specific embodiments described therein, it is to be understood that various modifications may be made in the construction without departing from the scope of the invention as defined in the appended claims.

It is claimed:

1. An adjustable spring-loaded splint comprising a pair of lower struts and a pair of upper struts, each member of the pair of lower struts being pivotably connected to a member of the pair of upper struts, said members of each pair being spaced apart a distance to accomodate limb parts distal and proximal to the limb joint, at least one of said struts having at one end a pivotably mounted head portion defining a cam surface, an adjustable spring means mounted within the strut pivotably connected to said cam surface-containing strut and biased into engagement with said cam surface, for applying a quantifiable force tending to align or approximate the cam surface-containing strut with the adjustable spring means and means provided said pair of upper struts and said pair of lower struts for securing holding therebetween said distal and proximal parts of a limb, said securing means comprising an elongate cuff member having on the outside thereof at least one velcro loop section spaced apart from at least one velcro hook section, said loop and hook sections each being followed by a zone therebetween containing both velcro hook and velcro loop sections, said zone between the spaced apart velcro hook and loop sections being comprised of an intermediate area constituted of a velcro loop section or hook section identical to the preceding section, flanked on each side by areas having a velcro loop section or a velcro hook section identical to the section of velcro hooks or loops that follows.

2. Securing means according to claim 1 wherein the cuff end section is provided on the outside thereof with stay-receiving means for receipt of a stay that extends substantially the width of the cuff and wherein the inside of the cuff is provided with a plurality of spaced apart stay-receiving means positioned along the length of the cuff for receipt of stays that extend substantially the width of the cuff.

* * * * *